(12) United States Patent
Hao et al.

(10) Patent No.: US 11,826,448 B2
(45) Date of Patent: *Nov. 28, 2023

(54) ZINC-ARGININE-CHLORIDE COMPLEX

(71) Applicant: Colgate-Palmolive Company, New York, NY (US)

(72) Inventors: Zhigang Hao, Bridgewater, NJ (US); Chi-Yuan Cheng, Hillsborough, NJ (US); Tatiana Brinzari, Piscataway, NJ (US); Long Pan, Somerset, NJ (US); Ravi Subramanyam, Belle Mead, NJ (US)

(73) Assignee: Colgate-Palmolive Company, New York, NY (US)

( * ) Notice: Subject to any disclaimer, the term of this patent is extended or adjusted under 35 U.S.C. 154(b) by 124 days.

This patent is subject to a terminal disclaimer.

(21) Appl. No.: 17/249,523

(22) Filed: Mar. 4, 2021

(65) Prior Publication Data

US 2021/0275416 A1  Sep. 9, 2021

Related U.S. Application Data

(63) Continuation of application No. 16/714,972, filed on Dec. 16, 2019, now Pat. No. 10,952,943.

(60) Provisional application No. 62/784,243, filed on Dec. 21, 2018.

(51) Int. Cl.
*A61K 8/27* (2006.01)
*A61K 8/34* (2006.01)
*A61K 8/44* (2006.01)
*A61Q 11/00* (2006.01)
*C07F 3/06* (2006.01)

(52) U.S. Cl.
CPC ............... *A61K 8/27* (2013.01); *A61K 8/345* (2013.01); *A61K 8/44* (2013.01); *A61Q 11/00* (2013.01); *C07F 3/06* (2013.01)

(58) Field of Classification Search
CPC ....................................................... A61K 8/27
See application file for complete search history.

(56) References Cited

U.S. PATENT DOCUMENTS

| | | |
|---|---|---|
| 3,535,421 A | 10/1970 | Briner et al. |
| 3,538,230 A | 11/1970 | Pader et al. |
| 3,678,154 A | 7/1972 | Widder et al. |
| 3,862,307 A | 1/1975 | Digiulio |
| 3,937,807 A | 2/1976 | Haefele |
| 3,941,818 A | 3/1976 | Abdel-Monem |
| 3,959,458 A | 5/1976 | Agricola et al. |
| 4,051,234 A | 9/1977 | Gieske et al. |
| 4,340,583 A | 7/1982 | Wason |
| 4,842,847 A | 6/1989 | Amjad |
| 4,866,161 A | 9/1989 | Sikes et al. |
| 4,885,155 A | 12/1989 | Parran, Jr. et al. |
| 5,004,597 A | 4/1991 | Majeti et al. |
| 5,061,815 A | 10/1991 | Leu |
| 5,188,821 A | 2/1993 | Gaffar et al. |
| 5,192,531 A | 3/1993 | Gaffar et al. |
| 6,121,315 A | 9/2000 | Nair et al. |
| 7,341,708 B1 | 3/2008 | Miroshnychenko et al. |
| 7,547,454 B2 | 6/2009 | Gupta |
| 8,652,495 B2 | 2/2014 | Maloney et al. |
| 9,498,421 B2 | 11/2016 | Liu et al. |
| 9,504,858 B2 | 11/2016 | Yuan et al. |
| 9,532,932 B2 | 1/2017 | Prencipe et al. |
| 9,572,756 B2 | 2/2017 | Liu et al. |
| 9,675,823 B2 | 6/2017 | Liu et al. |
| 9,718,843 B2 | 8/2017 | Fitzgerald et al. |
| 9,750,670 B2 | 9/2017 | Pan et al. |
| 9,757,316 B2 | 9/2017 | Pan et al. |
| 9,763,865 B2 | 9/2017 | Pan et al. |
| 9,775,792 B2 | 10/2017 | Liu et al. |
| 9,827,177 B2 | 11/2017 | Yuan et al. |
| 9,861,563 B2 | 1/2018 | Kilpatrick-Liverman et al. |
| 9,883,995 B2 | 2/2018 | Prencipe et al. |
| 9,901,523 B2 | 2/2018 | Xu et al. |
| 9,913,784 B2 | 3/2018 | Szewczyk et al. |
| 9,925,130 B2 | 3/2018 | Pan et al. |
| 9,943,473 B2 | 4/2018 | Pan et al. |
| 9,980,890 B2 | 5/2018 | Pan et al. |
| 9,993,407 B2 | 6/2018 | Liu et al. |
| 10,105,303 B2 | 10/2018 | Pan et al. |
| 10,130,571 B2 | 11/2018 | Szewczyk et al. |
| 10,188,112 B2 | 1/2019 | Hardy et al. |
| 10,195,125 B2 | 2/2019 | Pan et al. |
| 10,245,222 B2 | 4/2019 | Pan et al. |
| 10,485,742 B2 | 11/2019 | Patel et al. |
| 10,494,589 B2 | 12/2019 | Yuan et al. |
| 10,952,943 B2 * | 3/2021 | Hao .................. A61Q 11/00 |
| 2004/0198998 A1 | 10/2004 | Holerca et al. |

(Continued)

FOREIGN PATENT DOCUMENTS

| | | |
|---|---|---|
| CN | 101172956 | 5/2008 |
| EP | 0108937 | 9/1984 |

(Continued)

OTHER PUBLICATIONS

Hartwell et al., 1970, "Preparation and Characterization of Tyrosine and Lysine Metal Chelate Polyesters and Polyamides," Journal of the American Chemical Society 92(5):1284-1289.

International Search Report and Written Opinion of the International Searching Authority in International Application No. PCT/US2012/070498, dated Sep. 4, 2013.

International Search Report and Written Opinion of the International Searching Authority in International Application No. PCT/US2012/070525, dated Sep. 27, 2013.

International Search Report and Written Opinion of the International Searching Authority in International Application No. PCT/US2014/042947, dated Mar. 27, 2015.

*Primary Examiner* — Brian J Davis

(57) ABSTRACT

The disclosure provides a zinc-arginine complex, methods of making the same, and methods of using the same in oral care compositions.

17 Claims, 1 Drawing Sheet

(56) References Cited

U.S. PATENT DOCUMENTS

| | | |
|---|---|---|
| 2017/0121351 A1 | 5/2017 | Nawrocki et al. |
| 2018/0116924 A1 | 5/2018 | Prencipe et al. |
| 2018/0243193 A1 | 8/2018 | Pan et al. |
| 2018/0256468 A1 | 9/2018 | Liu et al. |
| 2019/0015310 A1 | 1/2019 | Pan et al. |
| 2019/0091117 A1 | 3/2019 | Szewczyk et al. |
| 2019/0104741 A1 | 4/2019 | Hardy et al. |
| 2019/0117536 A1 | 4/2019 | Pan et al. |
| 2019/0169034 A1 | 6/2019 | Dubovoy et al. |
| 2019/0175478 A1 | 6/2019 | Szewczyk et al. |
| 2019/0183766 A1 | 6/2019 | Pan et al. |

FOREIGN PATENT DOCUMENTS

| | | |
|---|---|---|
| EP | 1529775 | 5/2005 |
| GB | 2052978 | 2/1981 |
| JP | 2004-175790 | 6/2004 |
| WO | 2012/001337 | 1/2012 |
| WO | 2014/098825 | 6/2014 |
| WO | 2015/094254 | 6/2015 |

\* cited by examiner

ZINC-ARGININE-CHLORIDE COMPLEX

CROSS-REFERENCE TO RELATED APPLICATIONS

This application is a continuation of U.S. patent application Ser. No. 16/714,972, filed Dec. 16, 2019, which is a U.S. national application filed under 35 U.S.C. § 119(a) claiming priority to and the benefit of U.S. Provisional Application No. 62/784,243, filed on Dec. 21, 2018, the contents of which are hereby incorporated by reference in their entireties.

BACKGROUND OF THE INVENTION

Dental erosion involves demineralization and damage to the tooth structure due to acid attack from nonbacterial sources. Erosion is found initially in the enamel and, if unchecked, may proceed to the underlying dentin. Dental erosion may be caused or exacerbated by acidic foods and drinks, exposure to chlorinated swimming pool water, and regurgitation of gastric acids. The tooth enamel is a negatively charged surface, which naturally tends to attract positively charged ions such as hydrogen and calcium ions, while resisting negatively charged ions such as fluoride ions. Depending upon relative pH of surrounding saliva, the tooth enamel will lose or gain positively charged ions such as calcium ions. Generally saliva has a pH between 7.2 to 7.4. When the pH is lowered and concentration of hydrogen ions becomes relatively high, the hydrogen ions will replace the calcium ions in the enamel, forming hydrogen phosphate (phosphoric acid), which damages the enamel and creates a porous, sponge-like roughened surface. If saliva remains acidic over an extended period, then remineralization may not occur, and the tooth will continue to lose minerals, causing the tooth to weaken and ultimately to lose structure.

Dentinal hypersensitivity is acute, localized tooth pain in response to physical stimulation of the dentine surface as by thermal (hot or cold) osmotic, tactile combination of thermal, osmotic and tactile stimulation of the exposed dentin. Exposure of the dentine, which is generally due to recession of the gums, or loss of enamel, frequently leads to hypersensitivity. Dentinal tubules open to the surface have a high correlation with dentine hypersensitivity. Dentinal tubules lead from the pulp to the cementum. When the surface cementum of the tooth root is eroded, the dentinal tubules become exposed to the external environment. The exposed dentinal tubules provide a pathway for transmission of fluid flow to the pulpal nerves, the transmission induced by changes in temperature, pressure and ionic gradients.

Heavy metal ions, such as zinc, are resistant to acid attack. Zinc ranks above hydrogen in the electrochemical series, so that metallic zinc in an acidic solution will react to liberate hydrogen gas as the zinc passes into solution to form di-cations, $Zn^{2+}$. Zinc has been shown to have antibacterial properties in plaque and caries studies.

Soluble zinc salts, such as zinc citrate, have been used in dentifrice compositions, see, e.g., U.S. Pat. No. 6,121,315, but have several disadvantages. Zinc ions in solution impart an unpleasant, astringent mouthfeel, so formulations that provide effective levels of zinc, and also have acceptable organoleptic properties, have been difficult to achieve. Finally, the zinc ions will react with anionic surfactants such as sodium lauryl sulfate, thus interfering with foaming and cleaning. Zinc oxide and insoluble zinc salts, on the other hand, may do a poor job of delivering zinc to the teeth because of their insolubility.

While the prior art discloses the use of various oral compositions for the treatment of dentinal hypersensitivity, dental caries, and enamel erosion and demineralization, there is still a need for additional compositions and methods which provide improved performance in such treatments.

BRIEF SUMMARY OF THE INVENTION

It has now been discovered that zinc ions can form a particular soluble complex with the amino acid arginine. The complex comprises zinc, arginine, and chloride in a cationic coordination complex, optionally associated with an anion (e.g., a monovalent anion, such as a halide). When placed in formulation, this complex provides an effective concentration of zinc ions to the enamel, thereby protecting against erosion, reducing bacterial colonization and biofilm development, and providing enhanced shine to the teeth. Moreover, upon use, the formulation provides a precipitate that can plug the dentinal tubules, thereby reducing the sensitivity of the teeth. While providing efficient delivery of zinc in comparison to formulations with insoluble zinc salts, the formulations comprising the zinc-amino acid complex do not exhibit the poor taste and mouthfeel, poor fluoride delivery, and poor foaming and cleaning associated with conventional zinc-based oral care products using soluble zinc salts. The present disclosure provides a zinc-bis(arginine) complex (ZBA), for example, a zinc-bis(arginine)-bis(chloride) complex, formed from a mixture of zinc chloride and arginine. In some embodiments, the chemical structure of ZBA is $[Zn(arginine)_2Cl]^+Cl^-$. Any suitable monovalent or divalent anion may be used in combination with the cationic complex to form a charge-neutral salt. In aqueous solution, the complex may exist as the cationic coordination complex ($[Zn(arginine)_2X]^+$) in loose association with, or dissociated from, the anion. The complex may also be isolated as a solid salt, e.g., a crystal, optionally in mono- or dihydrate form.

In another aspect, the invention provides oral care compositions, for example mouthwash, oral gel or dentifrice compositions, that comprise the aforementioned zinc-arginine complexes. The compositions may optionally further comprise a fluoride source, a phosphate source, or any other suitable oral care actives or excipients. The compositions may be formulated in a suitable oral care formulation e.g., a conventional dentifrice, oral gel or mouthwash base, e.g., comprising one or more abrasives, surfactants, foaming agents, vitamins, polymers, enzymes, humectants, thickeners, antimicrobial agents, preservatives, flavorings, and/or colorants.

The invention further provides methods of using the compositions of the invention to reduce and inhibit acid erosion of the enamel, clean the teeth, reduce bacterially-generated biofilm and plaque, reduce gingivitis, inhibit tooth decay and formation of cavities, and reduce dentinal hypersensitivity, comprising applying a composition of the invention to the teeth.

The invention further provides methods of making the complexes and compositions of the invention comprising combining a zinc ion source (e.g., zinc chloride), arginine (e.g., arginine free base), and optionally an additional anion source (e.g., halide). For example, in some embodiments, the methods comprise the step of zinc chloride and arginine free base in a suitable anhydrous solvent, e.g., glycerin, optionally at a molar ratio of zinc to arginine of about 1:1 to 1:3, e.g., 1:2, and optionally isolating the complex thus formed as a solid; and further optionally admixing with other oral care composition ingredients.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings.

DETAILED DESCRIPTION OF THE INVENTION

Figure 1A:
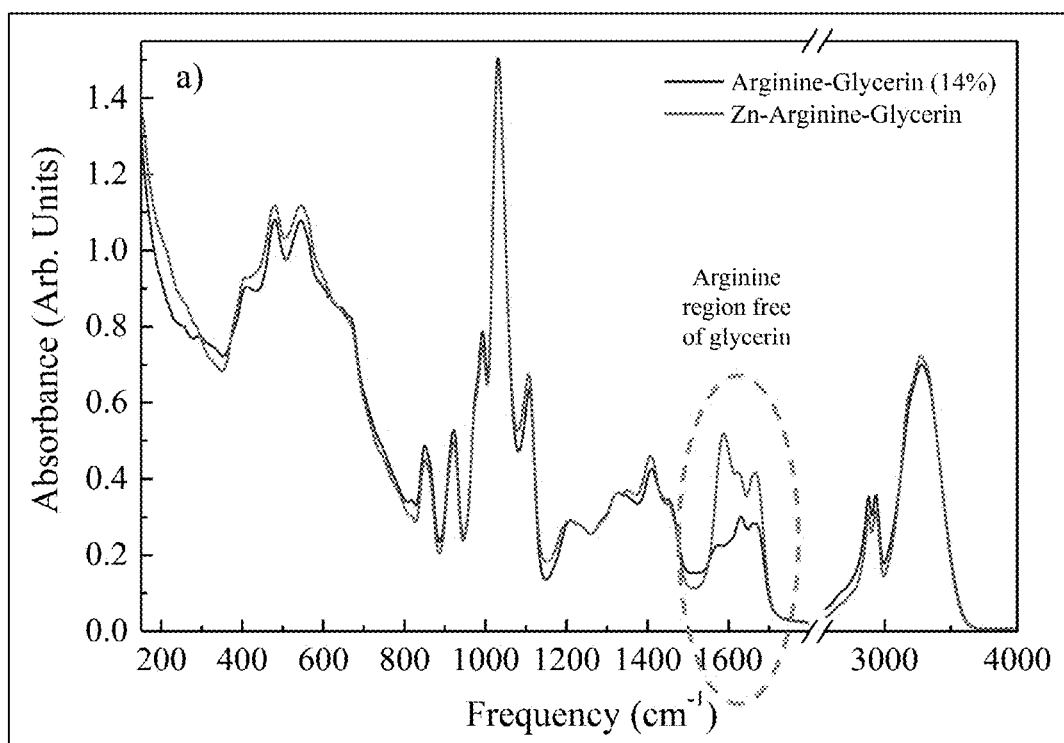
FIG. 1(a) depicts the FTIR spectrum obtained for the ZBA complex prepared according to Example 1 overlaid (grey) with the spectrum obtained for arginine and HCl (black).

The following description of the preferred embodiment(s) is merely exemplary in nature and is in no way intended to limit the invention, its application, or uses.

In a first aspect, the present disclosure provides, a zinc-arginine complex having the formula [Zn(arginine)$_2$X]$^+$X$^-$, wherein X is a monovalent anion (Complex 1). In further embodiments, the present disclosure provides:

1.1. Complex 1, wherein X is a halide (e.g., chloride, bromide, iodide or fluoride).
1.2. Complex 1, wherein X is chloride.
1.3. Complex 1, or 1.1 to 1.2, wherein the complex is formed by reacting a zinc ion source and arginine, in free or salt form, in a suitable solvent.
1.4. Complex 1.3, wherein the zinc ion source is selected from one or more of zinc oxide, zinc chloride, zinc sulfate, zinc nitrate, zinc phosphate, zinc hydroxide, zinc citrate, zinc lactate, zinc bromide, zinc iodide, and zinc acetate.
1.5. Complex 1.3 or 1.4, wherein the arginine is arginine free base.
1.6. Complex 1.3 or 1.4, wherein the arginine is arginine in salt form, e.g., arginine carbonate, arginine bicarbonate, arginine hydrochloride, arginine phosphate, arginine sulfate, arginine acetate, arginine citrate, or arginine nitrate.
1.7. Any of Complexes 1.3-1.6, wherein the suitable solvent comprises one or more of water, methanol, ethanol, propanol, isopropanol, butanol, ethylene glycol, propylene glycol, glycerin (a.k.a. glycerol), xylitol, erythritol, pentaerythritol, and diethylene glycol.
1.8. Complex 1.7, wherein the suitable solvent comprises glycerin, optionally a mixture of glycerin and water.
1.9. Any of Complexes 1.3-1.8, wherein the suitable solvent is anhydrous (e.g., the solvent comprises less than 5% water, or less than 4%, or less than 3%, or less than 2% or less than 1%, or less than 0.5%, each measured v/v).
1.10. Any of Complexes 1.3-1.8, wherein the zinc ion source and the arginine are combined in a molar ratio of 1:1 to 1:3, e.g., about 1:2.
1.11. Any of Complexes 1.3-1.8, wherein the complex is formed by reacting zinc chloride and arginine free base in anhydrous glycerin solvent, optionally, wherein the molar ratio of zinc chloride to arginine is about 1:2.
1.12. Complex 1, or any of 1.1-1.11, wherein the complex is solid form.
1.13. Complex 1, or any of 1.1-1.11, wherein the complex is in crystalline form.
1.14. Any of the foregoing complexes wherein the complex has a structure wherein the Zn cation is coordinated by two arginine ligands with two nitrogen atoms from alpha NH$_2$ groups of the two lysine ligands and two oxygen atoms from carboxylic groups of the two lysine ligands in an equatorial plane, having a distorted square-pyramidal geometry with the apical position occupied by a chlorine atom, to form a positive cation moiety, with which a chloride anion is combined to form an ionic salt.
1.15. Any of the foregoing complexes which forms a precipitate (e.g., a zinc oxide precipitate) upon increasing dilution with water.

In a second aspect, the present disclosure provides an oral care composition (Composition 2) comprising a zinc-bis (arginine) complex. In further embodiments, the present disclosure provides:

2.1. Composition 2, wherein the zinc-bis(arginine) complex has the formula Zn(arginine)$_2$X$_2$, wherein X is a monovalent anion (e.g., halide).
2.2. Composition 2, wherein the zinc-bis(arginine) complex has the formula [Zn(arginine)$_2$X]$^+$X$^-$, wherein X is a monovalent anion (e.g., halide).
2.3. Composition 2.1 or 2.2 wherein X is a halide (e.g., chloride, bromide, iodide or fluoride).
2.4. Composition 2.1, 2.2 or 2.3, wherein X is chloride.
2.5. Composition 2, or any of 2.1-2.4, wherein the complex is formed by reacting a zinc ion source and arginine, in free or salt form, in a suitable solvent.
2.6. Composition 2.5, wherein the zinc ion source is selected from one or more of zinc oxide, zinc chloride, zinc sulfate, zinc nitrate, zinc phosphate, zinc hydroxide, zinc citrate, zinc lactate, zinc bromide, zinc iodide, and zinc acetate.
2.7. Composition 2.5 or 2.6, wherein the arginine is arginine free base.
2.8. Composition 2.5 or 2.6, wherein the arginine is arginine in salt form, e.g., arginine carbonate, arginine bicarbonate, arginine hydrochloride, arginine phosphate, arginine sulfate, arginine acetate, arginine citrate, or arginine nitrate.
2.9. Any of Compositions 2.5-2.8, wherein the suitable solvent comprises one or more of water, methanol, ethanol, propanol, isopropanol, butanol, ethylene glycol, propylene glycol, glycerin (a.k.a. glycerol), xylitol, erythritol, pentaerythritol, and diethylene glycol.
2.10. Composition 2.9, wherein the suitable solvent comprises glycerin, optionally a mixture of glycerin and water.
2.11. Any of Compositions 2.5-2.10, wherein the suitable solvent is anhydrous (e.g., the solvent comprises less than 5% water, or less than 4%, or less than 3%, or less than 2% or less than 1%, or less than 0.5%, each measured v/v).
2.12. Any of Compositions 2.5-2.10, wherein the zinc ion source and the arginine are combined in a molar ratio of 1:1 to 1:3, e.g., about 1:2.
2.13. Any of Compositions 2.5-2.10, wherein the complex is formed by reacting zinc chloride and arginine free base in anhydrous glycerin solvent, optionally, wherein the molar ratio of zinc chloride to arginine is about 1:2.
2.14. Composition 2, or any of 2.1-2.13, wherein the complex is solid form.

2.15. Composition 2, or any of 2.1-2.13, wherein the complex is in crystalline form.
2.16. Composition 2, or any of 2.1-1.3, wherein the complex has a structure wherein a Zn cation is coordinated by two arginine ligands with two nitrogen atoms from alpha $NH_2$ groups of the two lysine ligands and two oxygen atoms from carboxylic groups of the two lysine ligands in an equatorial plane, having a distorted square-pyramidal geometry with the apical position occupied by a chlorine atom, to form a positive cation moiety, with which a chloride anion is combined to form an ionic salt
2.17. Any of the foregoing compositions wherein, upon dilution with water, the ZLC provides a zinc oxide precipitate.
2.18. Any of the foregoing compositions comprising Complex 1 or any of 1.1-1.15.
2.19. Any of the foregoing compositions comprising the complex in an amount of 0.05 to 40% by weight of the composition, e.g., from 0.05 to 20%, or from 0.05 to 15%, or from 0.05 to 10%, or from 0.5 to 10%, or from 0.5 to 5%, by weight of the composition.
2.20. Any of the foregoing compositions, wherein a total amount of zinc present in the composition is 0.05 to 10% by weight of the composition, e.g., from 0.05 to 5%, or from 0.05-3%, or from 0.5 to 3%, by weight of the composition.
2.21. Any of the foregoing compositions, wherein the composition comprises less than 10% water, e.g., less than 5% water, or less than 3%, or less than 2% or less than 1% water, by weight of the composition.
2.22. Any of the foregoing compositions, wherein the composition is a toothpaste, gel, mouthwash, powder, cream, strip, or gum.
2.23. Any of the foregoing compositions, wherein the composition is a toothpaste, gel or mouthwash.
2.24. Any of the foregoing compositions, further comprising zinc oxide, zinc citrate, or a combination thereof.
2.25. Composition 2.24, wherein the composition comprises from 0.1 to 3% zinc oxide and from 0.1 to 3% zinc citrate, e.g., about 1% zinc oxide and about 0.5% zinc citrate, by weight of the composition.
2.26. Composition 2.24 or 2.25, further comprising arginine, in free or salt form, in an amount of 1 to 5%, e.g., 1.5%, by weight of the composition.
2.27. Any of the foregoing compositions further comprising an effective amount of a fluoride ion source, e.g., providing 50 to 3000 ppm fluoride.
2.28. Any of the foregoing compositions further comprising an effective amount of fluoride, e.g., wherein the fluoride is a salt selected from stannous fluoride, sodium fluoride, potassium fluoride, sodium monofluorophosphate, sodium fluorosilicate, ammonium fluorosilicate, amine fluoride (e.g., N'-octadecyltrimethylendiamine-N,N,N'-tris(2-ethanol)-dihydrofluoride), ammonium fluoride, titanium fluoride, hexafluorosulfate, and combinations thereof.
2.29. Any of the preceding compositions comprising an effective amount of one or more alkali phosphate salts, e.g., sodium, potassium or calcium salts, e.g., selected from alkali dibasic phosphate and alkali pyrophosphate salts, e.g., alkali phosphate salts selected from sodium phosphate dibasic, potassium phosphate dibasic, dicalcium phosphate dihydrate, calcium pyrophosphate, tetrasodium pyrophosphate, tetrapotassium pyrophosphate, sodium tripolyphosphate, and mixtures of any of two or more of these, e.g., in an amount of 1-20%, e.g., 2-8%, e.g., ca. 5%, by weight of the composition.
2.30. Any of the foregoing compositions comprising buffering agents, e.g., sodium phosphate buffer (e.g., sodium phosphate monobasic and disodium phosphate).
2.31. Any of the foregoing compositions comprising a humectant, e.g., selected from glycerin, sorbitol, propylene glycol, polyethylene glycol, xylitol, and mixtures thereof, e.g. comprising at least 20%, e.g., 20-40%, e.g., 25-35% glycerin.
2.32. Any of the preceding compositions comprising one or more surfactants, e.g., selected from anionic, cationic, zwitterionic, and nonionic surfactants, and mixtures thereof, e.g., comprising an anionic surfactant, e.g., a surfactant selected from sodium lauryl sulfate, sodium ether lauryl sulfate, and mixtures thereof, e.g. in an amount of from about 0.3% to about 4.5% by weight, e.g. 1-2% sodium lauryl sulfate (SLS); and/or a zwitterionic surfactant, for example a betaine surfactant, for example cocamidopropyl betaine, e.g. in an amount of from about 0.1% to about 4.5% by weight, e.g. 0.5-2% cocamidopropyl betaine.
2.33. Any of the preceding compositions further comprising a viscosity modifying amount of one or more of polysaccharide gums, for example xanthan gum or carrageenan, silica thickener, and combinations thereof.
2.34. Any of the preceding compositions comprising gum strips or fragments.
2.35. Any of the preceding compositions further comprising flavoring, fragrance and/or coloring.
2.36. Any of the preceding compositions further comprising a physiologically or orally acceptable potassium salt, e.g., potassium nitrate or potassium chloride, in an amount effective to reduce dentinal sensitivity.
2.37. Any of the foregoing compositions further comprising an anionic polymer, e.g., a synthetic anionic polymeric polycarboxylate, e.g., wherein the anionic polymer is selected from 1:4 to 4:1 copolymers of maleic anhydride or acid with another polymerizable ethylenically unsaturated monomer; e.g., wherein the anionic polymer is a methyl vinyl ether/maleic anhydride (PVM/MA) copolymer having an average molecular weight (M.W.) of about 30,000 to about 1,000,000, e.g. about 300,000 to about 800,000, e.g., wherein the anionic polymer is about 1-5%, e.g., about 2%, of the weight of the composition.
2.38. Any of the preceding compositions further comprising a breath freshener, fragrance or flavoring.
2.39. Any of the foregoing compositions, wherein the pH of the composition is approximately neutral, e.g., from pH 6 to pH 8 e.g., about pH 7.
2.40. Any of the forgoing compositions for use to reduce and inhibit acid erosion of the enamel, clean the teeth, reduce bacterially-generated biofilm and plaque, reduce gingivitis, inhibit tooth decay and formation of cavities, and reduce dentinal hypersensitivity.

In a third aspect, the present disclosure provides a method (Method 3) of making a zinc-bis(arginine) complex having the formula $[Zn(arginine)_2X]^+X^-$, wherein X is a monovalent anion, wherein the method comprises combining a zinc ion source and arginine, in free or salt form, and an X source, in a suitable solvent. In further embodiments of this aspect, the present disclosure provides:

3.1. Method 3, wherein X is a halide (e.g., chloride, bromide, iodide or fluoride).
3.2. Method 3, wherein X is chloride.
3.3. Method 3, or 3.1 to 3.2, wherein the X source is the same as either the zinc ion source or the arginine (e.g., the X source is a zinc-X salt and/or the arginine is in the form of a salt comprising X).
3.4. Any of Method 3 or 3.1-3.3, wherein the zinc ion source is selected from one or more of zinc oxide, zinc chloride, zinc sulfate, zinc nitrate, zinc phosphate, zinc hydroxide, zinc citrate, zinc lactate, zinc bromide, zinc iodide, and zinc acetate.
3.5. Method 3.4, wherein the arginine is arginine free base.
3.6. Method 3.4 or 3.5, wherein the arginine is arginine in salt form, e.g., arginine carbonate, arginine bicarbonate, arginine hydrochloride, arginine phosphate, arginine sulfate, arginine acetate, arginine citrate, or arginine nitrate.
3.7. Any of Method 3 or 3.1-3.6, wherein the suitable solvent comprises one or more of water, methanol, ethanol, propanol, isopropanol, butanol, ethylene glycol, propylene glycol, glycerin (a.k.a. glycerol), xylitol, erythritol, pentaerythritol, and diethylene glycol.
3.8. Method 3.7, wherein the suitable solvent comprises glycerin, optionally a mixture of glycerin and water.
3.9. Any of Method 3 or 3.1-3.8, wherein the suitable solvent is anhydrous (e.g., the solvent comprises less than 5% water, or less than 4%, or less than 3%, or less than 2% or less than 1%, or less than 0.5%, each measured v/v).
3.10. Any of Method 3 or 3.1-3.9, wherein the zinc ion source and the arginine are combined in a molar ratio of 1:1 to 1:3, e.g., about 1:2.
3.11. Any of Method 3 or 3.1-3.10, wherein the method comprises combining zinc chloride and arginine free base in anhydrous glycerin solvent, optionally, wherein the molar ratio of zinc chloride to arginine is about 1:2.
3.12. Any of Method 3 or 3.1-3.11, further comprising isolating the complex.
3.13. Method 3.12, wherein the complex is isolated in solid form.
3.14. Method 3.13, wherein the complex is isolated in crystalline form.
3.15. Any of the foregoing Methods, wherein the complex has a structure wherein the Zn cation is coordinated by two arginine ligands with two nitrogen atoms from alpha $NH_2$ groups of the two lysine ligands and two oxygen atoms from carboxylic groups of the two lysine ligands in an equatorial plane, having a distorted square-pyramidal geometry with the apical position occupied by a chlorine atom, to form a positive cation moiety, with which a chloride anion is combined to form an ionic salt.
3.16. Any of Method 3 or 3.1-3.15, wherein the complex is Complex 1 or any of 1.1-1.15.

In another aspect, the present disclosure further provides methods to reduce and inhibit acid erosion of the enamel, clean the teeth, reduce bacterially-generated biofilm and plaque, reduce gingivitis, inhibit tooth decay and formation of cavities, and reduce dentinal hypersensitivity, comprising applying an effective amount of Complex 1, or any of 1.1-1.15, or Composition 2, or any of 2.1-2.40, to the oral cavity (e.g., the teeth), and optionally then rinsing with water or aqueous solution sufficient to trigger precipitation of zinc oxide from the composition.

In another aspect, the present disclosure further provides the use of zinc ion source and an arginine, in free or salt form, to make an oral care composition, e.g., Composition 2 or any of 2.1-2.40, which composition comprises a zinc-bis(arginine) complex, e.g., Complex 1 or any of 1.1-1.15. zinc amino acid complex.

Without intending to be bound by theory, it is believed that the formation of the zinc arginine complex proceeds via formation of the zinc halide then coordination of arginine residues around a central zinc.

In some embodiments, the complex comprises a zinc cation complexed with two arginine residues and one chloride residue to form a cationic coordination complex. For example, the complex may have the formula $[Zn(arginine)_2Cl]^+Cl^-$. In this complex, Zn cation is coordinated by two arginine ligands with two N atoms from $NH_2$ groups and O atoms from carboxylic groups in an equatorial plane. It displays a distorted square-pyramidal geometry with the apical position occupied by a $Cl^-$ atom. This novel structure gives rise to a positive cation moiety, to which a $Cl^-$ anion is combined to form an ionic salt.

The complexes of the present disclosure can be delivered in the form of any oral care formulations, for example a toothpaste, gel, mouthwash, powder, cream, strip, gum, or any other known in the art.

If the complex is delivered in the form of a mouthwash, a person desiring the benefits rinses with the stock solution and natural dilution of the stock solution by saliva will initiate the precipitation of the zinc. Alternatively, the person can mix the stock solution with appropriate amount of an aqueous diluent, and rinse with the mixture.

In another embodiment, the oral care composition may be prepared and immediately transferred into a retaining tray, such as those used in holding whitening gels, and the person can wear the tray for the effective period of time. The teeth that are in contact with the mixture will be treated. For use with retaining tray, the mixture can be in the form of a low-viscosity liquid or a gel.

In another embodiment, the stock solution, or a mixture of stock solution with water, is applied to the teeth in a gel formulation, e.g., wherein the gel can stay on the tooth for an extended period of time for effective treatment.

The benefits of the oral care compositions of the invention are numerous. By providing zinc ions and zinc containing compounds that can release zinc ions in oral cavities, the oral care compositions of the invention provide antimicrobial, antiplaque, anti-gingivitis, anti-malodor, anti-caries, and anti-calculus benefits. The occluding particles and the surface deposits are compounds containing zinc (particularly ZnO), as well as other zinc derivatives which can release zinc ions into oral cavities and provide the various benefits as recognized above. Additional benefits include but are not limited to anti-attachment, anti-periodontitis and anti-bone loss, as well as promotion of wound healing.

A second benefit is the anti-erosive properties of zinc ions, which form anti-erosive deposits on tooth surfaces through oxidation and hydrolysis. The surface deposits, as well as the occluding particles, can react with and neutralize acids, thus protecting the dental surface from the erosive effects of the acids. In this regard, the more surface depositions/occlusion the treatments lead to, the more efficacious the treatments are, and therefore zinc-arginine and zinc-lysine are preferred. It is also noted that when the surface deposits and occluding particles neutralize acids, beneficial zinc ions and amino acids (infra) can be released, providing oral care benefits other than anti-erosion.

A third benefit is anti-sensitivity benefit as a result of the occlusion. Occlusion of dentin tubules leads to sensitivity relief.

A fourth benefit is the benefit associated with arginine. Arginine provides multiple benefits, for example, it can lead to higher pH of the plaque and can provide anti-caries benefits.

In certain embodiments, the amount of the complex in the composition is 0.05 to 10% by weight of the composition. In certain embodiments, precursors, e.g., a zinc ion source and arginine, in free or salt form, are present in amounts such that when combined to from the zinc-arginine complex, the complex would be present in an amount of 0.05 to 10% by weight of the composition. In some embodiments, the amount of the complex is at least 0.1, at least 0.2, at least 0.3, at least 0.4, at least 0.5, at least 1, at least 2, at least 3, or at least 4 up to 10% by weight of the composition. In other embodiments, the amount of the complex is less than 9, less than 8, less than 7, less than 6, less than 5, less than 4, less than 3, less than 2, less than 1, less than 0.5 to 0.05% by weight of the composition. In other embodiments, the amounts are 0.05 to 5%, 0.05 to 4%, 0.05 to 3%, 0.05 to 2%, 0.1 to 5%, 0.1 to 4%, 0.1 to 3%, 0.1 to 2%, 0.5 to 5%, 0.5 to 4%, 0.5 to 3%, or 0.5 to 2% by weight of the composition.

In certain embodiments, zinc is present in the composition at an amount of 0.05 to 10% by weight of the composition. In other embodiments, the amount of zinc is at least 0.1, at least 0.2, at least 0.3, at least 0.4, at least 0.5, at least 1, at least 2, at least 3, or at least 4 up to 10% by weight of the composition. In other embodiments, the amount of the zinc is less than 9, less than 8, less than 7, less than 6, less than 5, less than 4, less than 3, less than 2, less than 1, less than 0.5 to 0.05% by weight of the composition. In other embodiments, the amounts are 0.05 to 5%, 0.05 to 4%, 0.05 to 3%, 0.05 to 2%, 0.1 to 5%, 0.1 to 4%, 0.1 to 3%, 0.1 to 2%, 0.5 to 5%, 0.5 to 4%, 0.5 to 3%, or 0.5 to 2% by weight of the composition.

In some embodiments, the arginine is present in the composition at an amount of 0.05 to 30% by weight. In other embodiments, the amount is at least 0.1, at least 0.2, at least 0.3, at least 0.4, at least 0.5, at least 1, at least 2, at least 3, at least 4, at least 5, at least 10, at least 15, at least 20 up to 30% by weight. In other embodiments, the amount is less than 30, less than 25, less than 20, less than 15, less than 10, less than 5, less than 4, less than 3, less than 2, or less than 1 down to 0.05% by weight of the composition.

In certain embodiments, the composition is anhydrous. By anhydrous, there is less than 5% by weight water, optionally less than 4, less than 3, less than 2, less than 1, less than 0.5, less than 0.1 down to 0% by weight water.

When provided in an anhydrous composition, precursors, e.g., zinc oxide or zinc chloride and arginine free base or arginine hydrochloride, will not significantly react to form the a zinc-arginine complex. When contacted with a sufficient amount of water, which can be in the water using for carrying out the brushing of the teeth, the zinc ion source and arginine may react in the resulting aqueous solution or suspension to form a zinc arginine complex, e.g., Complex 1, et seq.

Fluoride Ion Source: The oral care compositions may further include one or more fluoride ion sources, e.g., soluble fluoride salts. A wide variety of fluoride ion-yielding materials can be employed as sources of soluble fluoride in the present compositions. Examples of suitable fluoride ion-yielding materials are found in U.S. Pat. No. 3,535,421, to Briner et al.; U.S. Pat. No. 4,885,155, to Parran, Jr. et al. and U.S. Pat. No. 3,678,154, to Widder et al. Representative fluoride ion sources include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In certain embodiments the fluoride ion source includes stannous fluoride, sodium fluoride, sodium monofluorophosphate as well as mixtures thereof. In certain embodiments, the oral care composition of the invention may also contain a source of fluoride ions or fluorine-providing ingredient in amounts sufficient to supply about 25 ppm to about 25,000 ppm of fluoride ions, generally at least about 500 ppm, e.g., about 500 to about 2000 ppm, e.g., about 1000 to about 1600 ppm, e.g., about 1450 ppm. The appropriate level of fluoride will depend on the particular application. A toothpaste for general consumer use would typically have about 1000 to about 1500 ppm, with pediatric toothpaste having somewhat less. A dentifrice or coating for professional application could have as much as about 5,000 or even about 25,000 ppm fluoride. Fluoride ion sources may be added to the compositions of the invention at a level of about 0.01 wt. % to about 10 wt. % in one embodiment or about 0.03 wt. % to about 5 wt. %, and in another embodiment about 0.1 wt. % to about 1 wt. % by weight of the composition in another embodiment. Weights of fluoride salts to provide the appropriate level of fluoride ion will obviously vary based on the weight of the counterion in the salt.

Abrasives: The compositions of the invention, e.g. Composition 1 et seq. include silica abrasives, and may comprise additional abrasives, e.g., a calcium phosphate abrasive, e.g., tricalcium phosphate ($Ca_3(PO_4)_2$), hydroxyapatite ($Ca_{10}(PO_4)_6(OH)_2$), or dicalcium phosphate dihydrate ($CaHPO_4.2H_2O$, also sometimes referred to herein as DiCal) or calcium pyrophosphate; calcium carbonate abrasive; or abrasives such as sodium metaphosphate, potassium metaphosphate, aluminum silicate, calcined alumina, bentonite or other siliceous materials, or combinations thereof.

Other silica abrasive polishing materials useful herein, as well as the other abrasives, generally have an average particle size ranging between about 0.1 and about 30 microns, about between 5 and about 15 microns. The silica abrasives can be from precipitated silica or silica gels, such as the silica xerogels described in U.S. Pat. No. 3,538,230, to Pader et al. and U.S. Pat. No. 3,862,307, to Digiulio. Particular silica xerogels are marketed under the trade name Syloid® by the W. R. Grace & Co., Davison Chemical Division. The precipitated silica materials include those marketed by the J. M. Huber Corp. under the trade name Zeodent®, including the silica carrying the designation Zeodent 115 and 119. These silica abrasives are described in U.S. Pat. No. 4,340,583, to Wason. In certain embodiments, abrasive materials useful in the practice of the oral care compositions in accordance with the invention include silica gels and precipitated amorphous silica having an oil absorption value of less than about 100 cc/100 g silica and in the range of about 45 cc/100 g to about 70 cc/100 g silica. Oil absorption values are measured using the ASTA Rub-Out Method D281. In certain embodiments, the silicas are colloidal particles having an average particle size of about 3 microns to about 12 microns, and about 5 to about 10 microns. Low oil absorption silica abrasives particularly useful in the practice of the invention are marketed under the trade designation Sylodent XWA® by Davison Chemical Division of W.R. Grace & Co., Baltimore, Md. 21203. Sylodent 650 XWA®, a silica hydrogel composed of particles of colloidal silica having a water content of 29% by weight averaging about 7 to about 10 microns in diameter, and an oil absorption of less than about 70 cc/100 g of silica is an example of a low oil absorption silica abrasive useful in the practice of the present invention.

Foaming agents: The oral care compositions of the invention also may include an agent to increase the amount of foam that is produced when the oral cavity is brushed. Illustrative examples of agents that increase the amount of foam include, but are not limited to polyoxyethylene and certain polymers including, but not limited to, alginate polymers. The polyoxyethylene may increase the amount of foam and the thickness of the foam generated by the oral care carrier component of the present invention. Polyoxyethylene is also commonly known as polyethylene glycol ("PEG") or polyethylene oxide. The polyoxyethylenes suitable for this invention will have a molecular weight of about 200,000 to about 7,000,000. In one embodiment the molecular weight will be about 600,000 to about 2,000,000 and in another embodiment about 800,000 to about 1,000,000. Polyox® is the trade name for the high molecular weight polyoxyethylene produced by Union Carbide. The polyoxyethylene may be present in an amount of about 1% to about 90%, in one embodiment about 5% to about 50% and in another embodiment about 10% to about 20% by weight of the oral care carrier component of the oral care compositions of the present invention. Where present, the amount of foaming agent in the oral care composition (i.e., a single dose) is about 0.01 to about 0.9% by weight, about 0.05 to about 0.5% by weight, and in another embodiment about 0.1 to about 0.2% by weight.

Surfactants: The compositions useful in the invention may contain anionic surfactants, for example:
  i. water-soluble salts of higher fatty acid monoglyceride monosulfates, such as the sodium salt of the monosulfated monoglyceride of hydrogenated coconut oil fatty acids such as sodium N-methyl N-cocoyl taurate, sodium cocomonoglyceride sulfate,
  ii. higher alkyl sulfates, such as sodium lauryl sulfate,
  iii. higher alkyl-ether sulfates, e.g., of formula $CH_3(CH_2)_mCH_2(OCH_2CH_2)_nOSO_3X$, wherein m is 6-16, e.g., 10, n is 1-6, e.g., 2, 3 or 4, and X is Na or K, for example sodium laureth-2 sulfate $(CH_3(CH_2)_{10}CH_2(OCH_2CH_2)_2OSO_3Na)$.
  iv. higher alkyl aryl sulfonates such as sodium dodecyl benzene sulfonate (sodium lauryl benzene sulfonate)
  v. higher alkyl sulfoacetates, such as sodium lauryl sulfoacetate (dodecyl sodium sulfoacetate), higher fatty acid esters of 1,2 dihydroxy propane sulfonate, sulfocolaurate (N-2-ethyl laurate potassium sulfoacetamide) and sodium lauryl sarcosinate.

By "higher alkyl" is meant, e.g., $C_{6-30}$ alkyl. In particular embodiments, the anionic surfactant is selected from sodium lauryl sulfate and sodium ether lauryl sulfate. The anionic surfactant may be present in an amount which is effective, e.g., >0.01% by weight of the formulation, but not at a concentration which would be irritating to the oral tissue, e.g., <10%, and optimal concentrations depend on the particular formulation and the particular surfactant. For example, concentrations used or a mouthwash are typically on the order of one tenth that used for a toothpaste. In one embodiment, the anionic surfactant is present in a toothpaste at from about 0.3% to about 4.5% by weight, e.g., about 1.5%. The compositions of the invention may optionally contain mixtures of surfactants, e.g., comprising anionic surfactants and other surfactants that may be anionic, cationic, zwitterionic or nonionic. Generally, surfactants are those which are reasonably stable throughout a wide pH range. Surfactants are described more fully, for example, in U.S. Pat. No. 3,959,458, to Agricola et al.; U.S. Pat. No. 3,937,807, to Haefele; and U.S. Pat. No. 4,051,234, to Gieske et al. In certain embodiments, the anionic surfactants useful herein include the water-soluble salts of alkyl sulfates having about 10 to about 18 carbon atoms in the alkyl radical and the water-soluble salts of sulfonated monoglycerides of fatty acids having about 10 to about 18 carbon atoms. Sodium lauryl sulfate, sodium lauroyl sarcosinate and sodium coconut monoglyceride sulfonates are examples of anionic surfactants of this type. In a particular embodiment, the composition of the invention, e.g., Composition 1, et seq., comprises sodium lauryl sulfate.

The surfactant or mixtures of compatible surfactants can be present in the compositions of the present invention in about 0.1% to about 5.0%, in another embodiment about 0.3% to about 3.0% and in another embodiment about 0.5% to about 2.0% by weight of the total composition.

Tartar control agents: In various embodiments of the present invention, the compositions comprise an anticalculus (tartar control) agent. Suitable anticalculus agents include without limitation phosphates and polyphosphates (for example pyrophosphates), polyaminopropanesulfonic acid (AMPS), hexametaphosphate salts, zinc citrate trihydrate, polypeptides, polyolefin sulfonates, polyolefin phosphates, diphosphonates. The invention thus may comprise phosphate salts. In particular embodiments, these salts are alkali phosphate salts, i.e., salts of alkali metal hydroxides or alkaline earth hydroxides, for example, sodium, potassium or calcium salts. "Phosphate" as used herein encompasses orally acceptable mono- and polyphosphates, for example, $P_{1-6}$ phosphates, for example monomeric phosphates such as monobasic, dibasic or tribasic phosphate; dimeric phosphates such as pyrophosphates; and multimeric phosphates, e.g., sodium hexametaphosphate. In particular examples, the selected phosphate is selected from alkali dibasic phosphate and alkali pyrophosphate salts, e.g., selected from sodium phosphate dibasic, potassium phosphate dibasic, dicalcium phosphate dihydrate, calcium pyrophosphate, tetrasodium pyrophosphate, tetrapotassium pyrophosphate, sodium tripolyphosphate, and mixtures of any of two or more of these. In a particular embodiment, for example the compositions comprise a mixture of tetrasodium pyrophosphate $(Na_4P_2O_7)$, calcium pyrophosphate $(Ca_2P_2O_7)$, and sodium phosphate dibasic $(Na_2HPO_4)$, e.g., in amounts of ca. 3-4% of the sodium phosphate dibasic and ca. 0.2-1% of each of the pyrophosphates. In another embodiment, the compositions comprise a mixture of tetrasodium pyrophosphate (TSPP) and sodium tripolyphosphate (STPP)$(Na_5P_3O_{10})$, e.g., in proportions of TSPP at about 1-2% and STPP at about 7% to about 10%. Such phosphates are provided in an amount effective to reduce erosion of the enamel, to aid in cleaning the teeth, and/or to reduce tartar buildup on the teeth, for example in an amount of 2-20%, e.g., ca. 5-15%, by weight of the composition.

Flavoring Agents: The oral care compositions of the invention may also include a flavoring agent. Flavoring agents which are used in the practice of the present invention include, but are not limited to, essential oils as well as various flavoring aldehydes, esters, alcohols, and similar materials. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Certain embodiments employ the oils of peppermint and spearmint. The flavoring agent may be incorporated in the oral composition at a concentration of about 0.1 to about 5% by weight e.g. about 0.5 to about 1.5% by weight.

Polymers: The oral care compositions of the invention may also include additional polymers to adjust the viscosity of the formulation or enhance the solubility of other ingredients. Such additional polymers include polyethylene glycols, polysaccharides (e.g., cellulose derivatives, for example carboxymethyl cellulose, or polysaccharide gums, for example xanthan gum or carrageenan gum). Acidic polymers, for example polyacrylate gels, may be provided in the form of their free acids or partially or fully neutralized water soluble alkali metal (e.g., potassium and sodium) or ammonium salts.

Silica thickeners, which form polymeric structures or gels in aqueous media, may be present. Note that these silica thickeners are physically and functionally distinct from the particulate silica abrasives also present in the compositions, as the silica thickeners are very finely divided and provide little or no abrasive action. Other thickening agents are carboxyvinyl polymers, carrageenan, hydroxyethyl cellulose and water soluble salts of cellulose ethers such as sodium carboxymethyl cellulose and sodium carboxymethyl hydroxyethyl cellulose. Natural gums such as karaya, gum arabic, and gum tragacanth can also be incorporated. Colloidal magnesium aluminum silicate can also be used as component of the thickening composition to further improve the composition's texture. In certain embodiments, thickening agents in an amount of about 0.5% to about 5.0% by weight of the total composition are used.

The compositions of the invention may include an anionic polymer, for example in an amount of from about 0.05 to about 5%. Such agents are known generally for use in dentifrice, although not for this particular application, useful in the present invention are disclosed in U.S. Pat. Nos. 5,188,821 and 5,192,531; and include synthetic anionic polymeric polycarboxylates, such as 1:4 to 4:1 copolymers of maleic anhydride or acid with another polymerizable ethylenically unsaturated monomer, preferably methyl vinyl ether/maleic anhydride having a molecular weight (M.W.) of about 30,000 to about 1,000,000, most preferably about 300,000 to about 800,000. These copolymers are available for example as Gantrez. e.g., AN 139 (M.W. 500,000), AN 119 (M.W. 250,000) and preferably S-97 Pharmaceutical Grade (M.W. 700,000) available from ISP Technologies, Inc., Bound Brook, N.J. 08805. The enhancing agents when present are present in amounts ranging from about 0.05 to about 3% by weight. Other operative polymers include those such as the 1:1 copolymers of maleic anhydride with ethyl acrylate, hydroxyethyl methacrylate, N-vinyl-2-pyrollidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone. Suitable generally, are polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrylacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers contain sufficient carboxylic salt groups for water-solubility. A further class of polymeric agents includes a composition containing homopolymers of substituted acrylamides and/or homopolymers of unsaturated sulfonic acids and salts thereof, in particular where polymers are based on unsaturated sulfonic acids selected from acrylamidoalykane sulfonic acids such as 2-acrylamide 2 methylpropane sulfonic acid having a molecular weight of about 1,000 to about 2,000,000, described in U.S. Pat. No. 4,842,847, Jun. 27, 1989 to Zahid. Another useful class of polymeric agents includes polyamino acids containing proportions of anionic surface-active amino acids such as aspartic acid, glutamic acid and phosphoserine, e.g. as disclosed in U.S. Pat. No. 4,866,161 Sikes et al.

Water: The oral compositions may comprise significant levels of water. Water employed in the preparation of commercial oral compositions should be deionized and free of organic impurities. The amount of water in the compositions includes the free water which is added plus that amount which is introduced with other materials.

Humectants: Within certain embodiments of the oral compositions, it is also desirable to incorporate a humectant to prevent the composition from hardening upon exposure to air. Certain humectants can also impart desirable sweetness or flavor to dentifrice compositions. Suitable humectants include edible polyhydric alcohols such as glycerine, sorbitol, xylitol, propylene glycol as well as other polyols and mixtures of these humectants. In one embodiment of the invention, the principal humectant is glycerin, which may be present at levels of greater than 25%, e.g. 25-35% about 30%, with 5% or less of other humectants.

Other optional ingredients: In addition to the above-described components, the embodiments of this invention can contain a variety of optional dentifrice ingredients some of which are described below. Optional ingredients include, for example, but are not limited to, adhesives, sudsing agents, flavoring agents, sweetening agents, additional anti-plaque agents, abrasives, and coloring agents. These and other optional components are further described in U.S. Pat. No. 5,004,597, to Majeti; U.S. Pat. No. 3,959,458 to Agricola et al. and U.S. Pat. No. 3,937,807, to Haefele, all being incorporated herein by reference.

Unless stated otherwise, all percentages of composition components given in this specification are by weight based on a total composition or formulation weight of 100%.

Unless otherwise specifically identified, the ingredients for use in the compositions and formulations of the present invention are preferably orally acceptable ingredients. By "orally acceptable" is meant suitable for use in a formulation for intra-oral application to the oral cavity and/or teeth.

The compositions and formulations as provided herein are described and claimed with reference to their ingredients, as is usual in the art. As would be evident to one skilled in the art, the ingredients may in some instances react with one another, so that the true composition of the final formulation may not correspond exactly to the ingredients listed. Thus, it should be understood that the invention extends to the product of the combination of the listed ingredients.

Example 1—Synthesis and Characterization of Anhydrous Liquid ZBA Complex

The general reaction for formation of ZBA according to this method is as follows:

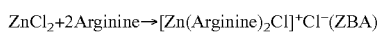

$$ZnCl_2 + 2\,Arginine \rightarrow [Zn(Arginine)_2Cl]^+Cl^- (ZBA)$$

Glycerin (400 g) is combined with zinc chloride (48.11 g) and L-arginine free base (123.00 g) in a 2 liter reaction vessel. The mixture is stirred overnight with a mechanical stirrer set to 800 rpm. The theoretical ZBA concentration in glycerin is 30% (w/w) based on the ingredients as-combined. A sample of the resulting mixture is then analyzed using liquid chromatography-mass spectrometry (LC-MS), carbon-13 nuclear magnetic resonance (NMR) spectroscopy, and Fourier-transform infrared (FTIR) spectroscopy, as described further below.

LC-MS: LC-MS analysis is performed using an AB Sciex tandem mass spectrometer (AB Sciex LLC, Framingham, Mass., USA) equipped with an electrospray ionization (ESI) interface and an Agilent 1260 capillary LC system (Agilent Model 1260, Agilent Technologies, Palo Alto, Calif., USA). The capillary LC system is equipped with a capillary binary pump (Model G1376A), a DAD detector (G1315C), a micro vacuum degasser (Model G4225A), a thermostatted column compartment (Model G1316A). The capillary pump is set under the micro-flow mode. The LC separation is achieved using an Agilent Zorbax SB-Aq column with 2.1 mm i.d.×50 mm dimension and 3.5 μm particle size (Agilent Technologies, Palo Alto, Calif., USA Part No. 871700-914). The mobile phase is 50:50 methanol/water run at a flow rate of 70 μL/min, with an injected volume of 1 μL. The AB Sciex tandem mass spectrometer is operated in the positive-ion mode with nitrogen (>99.99%) as the curtain gas (10 psi), and as the ion source gas 1 and 2 (also 10 psi). ESI voltage is set at 5.5 kV, with declustering and entrance potential set at 80 V and 5.5 V, respectively. The temperature of the ionization interface is maintained at 550° C. For total ion count (TIC) mode, the MS screen range is from 100 to 700 m/z. Data is acquired with an Analyst software 1.6.2 system (AB Sciex LLC, Framingham, Mass., USA).

The sample of the ZBA solution is diluted to 1000 ppm with methanol, and a sample of this is then injected into the LCMS instrument. One LC peak elutes at a retention time of 4.48 to 5.50 minutes. The zinc complex with the typical zinc isotopic triplets is identified as a cluster showing m/z 410.4, 412.5 and 414.4. One mole of neutral HCl is eliminated by fragmentation when the ZBA coordination complex ([Zn (arginine)$_2$Cl]$^+$) proceeds through the electrospray ionization. The obtained mass ions are thus consistent with the structure of the neutral complex [Zn(arg)2]+H$^+$.

NMR: $^{13}$C NMR studies are performed on a Bruker Avance spectrometer (Bruker-Biospin, Billerica, Mass., US) with a 5 mm BBI probe operating at 500.0 MHz for $^1$H and 125.7 MHz for $^{13}$C in glycerin at 25° C. All $^{13}$C NMR spectra were acquired using a $^1$H decoupling sequence ("zgig" from Bruker pulse-program library) with a repetition time of 15 sec and 4096 transients.

The neat ZBA in glycerin solution (30% w/w) is directly transferred into a 5 mm NMR tube for analysis. The spectrum obtained from L-arginine free base dissolved in glycerin at 14% w/w is obtained for comparison. In the ZBA spectrum, the chemical shift of the carbonyl carbon is located at 183 ppm as a single peak. In contrast, the arginine spectrum shows the carbonyl carbon at 178 ppm. These results are consistent with the carboxyl group of arginine in the ZBA complex as coordinated to the zinc ion center.

FTIR: Infrared spectra are collected using a Bruker Vertex 70 FTIR spectrometer equipped with a GladiATR diamond ATR accessory (Pike technologies, Madison, Wis.). The spectral range is 80-4000 cm$^{-1}$ and a resolution of 4 cm$^{-1}$ is used.

Figure 1B:
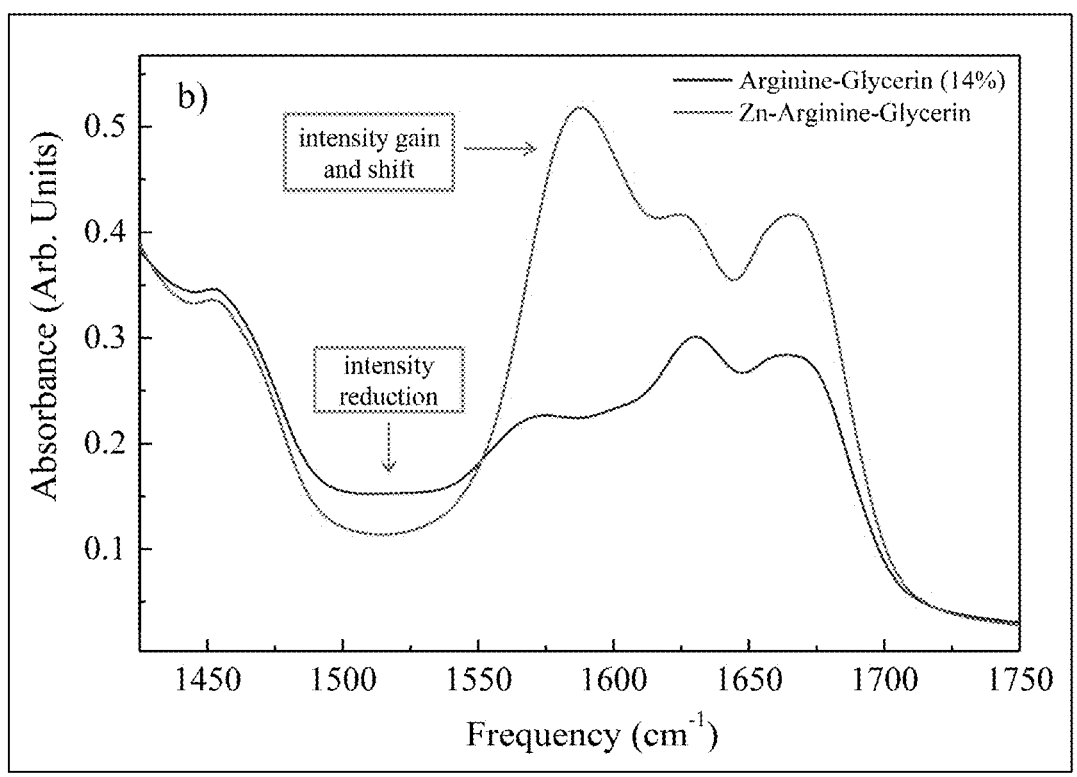
FIG. 1(b) shows the same spectra magnified in the region from 1400 to 1750 cm$^{-1}$.

FIG. 1(a) displays an overlay of the FTIR spectrum obtained from the neat ZBA in glycerin solution (30% w/w) compared to the FTIR spectrum of L-arginine and HCl (1:1 molar ratio) dissolved in glycerin (14% w/w arginine in glycerin). The arginine region around 1600 cm$^{-1}$ is free of overlap from glycerin spectrum and therefore, presents the best region to compare the two samples. FIG. 1(b) shows a close-up view of the arginine vibrational bands. As can be seen, in the presence of zinc $NH_2$ and $COO^-$ bands near 1590 cm$^{-1}$ display intensity gain (primarily due to $NH_2$ band) and shift in energy as compared to the free arginine. In addition, the $NH_3^+$ band of free arginine near 1520 cm$^{-1}$ exhibits a reduction in intensity. Taken together these data are consistent with the coordination of arginine to zinc ion in the ZBA complex. The bands assignment in glycerin is done based on the previously studied aqueous solutions.

Computational Modeling: A computer calculation is done at the B3LYP and M06 levels of density functional theory. Geometry optimizations and harmonic frequency calculations are performed at the B3LYP/BS1 level in aqueous solution using the SMD solvation model, BS1 designating a mixed basis set of SDD for zinc and 6-31G(d,p) for other atoms. The B3LYP/BS1-calculated harmonic frequencies are then used to obtain zero-point energy-corrected Gibbs free energies at 298.15 K and 1 atm. The calculation is performed with Gaussian 09.

The computational study indicates the following reaction is favorable:

$$[ZnCl(H_2O)_4]^+(aq) + Arg(aq) + HArg^+(aq) \rightarrow$$
$$[Zn(Arg)_2Cl]^+(aq) + 3H_2O(l) + H_3O^+(aq)$$

$\Delta G^0 = -6.6$ kcal/mol, $K_{eq}$ 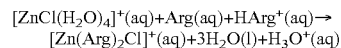 $= 6.9 \times 10^4$

Example 2: Biological Efficacy Evaluation

Wound healing efficacy is determined by incubating a monolayer cell culture with ZBA.

Briefly, a keratinocyte cell line (Hacat) was cultured with full confluency in a 24 well plate. The cells are then scratched horizontally and vertically with a pipet tips to generate a wound. The cells are washed twice with 1 mL of PBS buffer, then full culture medium (supplemented with 10% FBS and 1% antibiotic) is added to the scratched cells. The ZBA solution obtained from Example 1 is diluted with full culture medium at a concentration of 5 ppm or 50 ppm. Culture wells are incubated at 37° C. at 5% $CO_2$ for up to 72 hours with either the ZBA medium mixture or with medium alone. The area of the scratches is then compared by light microscopy at different time points up to 72 hrs.

The results show that culture treated with the ZBA solution of Example 1 produces greater cell migration and faster proliferation compared to medium alone. In addition, in the presence of ZBA, the morphology of the cells adjacent to the wound is improved.

Unless otherwise specified, all percentages and amounts expressed herein and elsewhere in the specification should be understood to refer to percentages by weight. The amounts given are based on the active weight of the material.

The invention claimed is:

1. An oral care composition comprising a zinc-bis(arginine) complex having the formula [Zn(arginine)$_2$X]$^+$X$^-$, wherein X is a monovalent anion wherein the complex is formed by combining a zinc ion source and arginine, in free or salt form, in a dentifrice or oral gel base comprising glycerol.

2. The composition of claim 1, wherein X is chloride.

3. The composition of claim 1, wherein the zinc ion source is selected from one or more of zinc oxide, zinc chloride, zinc sulfate, zinc nitrate, zinc phosphate, zinc hydroxide, zinc citrate, zinc lactate, zinc bromide, zinc iodide, and zinc acetate.

4. The composition of claim 1, wherein the arginine is arginine in salt form selected from arginine carbonate, arginine bicarbonate, arginine hydrochloride, arginine phosphate, arginine sulfate, arginine acetate, arginine citrate, and arginine nitrate.

5. The composition of claim 1, wherein the dentifrice or oral gel base further comprises one or more of water, propylene glycol, xylitol, and erythritol.

6. The composition of claim 5, wherein the dentifrice or oral gel base comprises a mixture of glycerin and water.

7. The composition of claim 1, wherein the complex is formed by combining zinc chloride and arginine free base in the dentifrice or oral gel base, optionally, wherein the molar ratio of zinc chloride to arginine is about 1:2.

8. The composition of claim 1, wherein the composition is a toothpaste, gel, mouthwash, powder, cream, strip, or gum.

9. A method of making an oral care composition comprising a zinc-bis(arginine) complex having the formula $[Zn(arginine)_2X]^+X^-$, wherein X is a monovalent anion, wherein the method comprises combining a zinc ion source and arginine, in free or salt form, and an X source, in a dentifrice or oral gel base comprising glycerol.

10. The method of claim 9, wherein X is halide.

11. The method of claim 9, wherein the method comprises combining zinc chloride and arginine free base in the dentifrice or oral gel base comprising glycerol, optionally, wherein the molar ratio of zinc chloride to arginine is about 1:2.

12. A method to reduce and inhibit acid erosion of the enamel, clean the teeth, reduce bacterially-generated biofilm and plaque, reduce gingivitis, inhibit tooth decay and formation of cavities, and reduce dentinal hypersensitivity, comprising applying an effective amount of the complex according to claim 1 to the oral cavity.

13. The method of claim 9, wherein the zinc ion source is selected from one or more of zinc oxide, zinc chloride, zinc sulfate, zinc nitrate, zinc phosphate, zinc hydroxide, zinc citrate, zinc lactate, zinc bromide, zinc iodide, and zinc acetate.

14. The method of claim 9, wherein the arginine is arginine in salt form selected from arginine carbonate, arginine bicarbonate, arginine hydrochloride, arginine phosphate, arginine sulfate, arginine acetate, arginine citrate, and arginine nitrate.

15. The method of claim 9, wherein the dentifrice or oral gel base further comprises one or more of water, propylene glycol, xylitol, and erythritol.

16. The method of claim 15, wherein the dentifrice or oral gel base comprises a mixture of glycerin and water.

17. A method to promote wound healing in the oral cavity comprising apply an effective amount of the composition according to claim 1 to the oral cavity.

* * * * *